(12) United States Patent
Spinner et al.

(10) Patent No.: US 8,489,381 B1
(45) Date of Patent: *Jul. 16, 2013

(54) METHOD AND SYSTEM FOR SIMULATING TEST INSTRUMENTS AND INSTRUMENT FUNCTIONS

(75) Inventors: Robert Spinner, East Northport, NY (US); Eli Levi, Dix Hills, NY (US); William Harold Leippe, Coram, NY (US); Emery Korpi, Syosset, NY (US); Michael Lai, Smithtown, NY (US); James Kuveikis, Bohemia, NY (US); Richard E. Chalmers, Northport, NY (US); Richard Engel, Ridge, NY (US); Peter F. Britch, Miller Place, NY (US); William Biagiotti, St. James, NY (US); David Howell, Smithfield, VA (US)

(73) Assignee: Advanced Testing Technologies, Inc., Hauppauge, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/411,697

(22) Filed: Mar. 5, 2012

Related U.S. Application Data

(63) Continuation of application No. 11/514,717, filed on Sep. 1, 2006, now Pat. No. 8,131,529.

(60) Provisional application No. 60/713,443, filed on Sep. 1, 2005.

(51) Int. Cl.
  *G06F 9/44* (2006.01)
  *G06F 13/10* (2006.01)
  *G06F 13/12* (2006.01)

(52) U.S. Cl.
  USPC .......................... 703/20; 702/121

(58) Field of Classification Search
  CPC ................................ G06F 17/5022
  USPC ............. 703/13, 20, 21, 23; 702/108, 121
  See application file for complete search history.

(56) References Cited

U.S. PATENT DOCUMENTS 6,311,149 B1 * 10/2001 Ryan et al. ............... 703/21

\* cited by examiner

*Primary Examiner* — Kamini S Shah
*Assistant Examiner* — Luke Osborne
(74) *Attorney, Agent, or Firm* — Brian Roffe

(57) ABSTRACT

Method and system to configure a common set of electronic components using software in order to simulate different electronic, mechanical and/or electro-mechanical instruments or instrument functions. For each instrument function or traditional mode of operation to be simulated, software models are created which when directed to the electronic components, cause the electronic components to respond to input in the same manner that the actual, traditional physical instrument would respond to satisfy the same test requirement input. The software models are preferably stored in a model repository which is searchable to enable a user to select the instrument function or traditional mode of operation to be simulated with the corresponding model being provided to the electronic components. Once the model, i.e., a function for each synthetic element, is downloaded and the electronic components configured according to the model functions, testing of the assemblies or other UUTs can begin.

21 Claims, 5 Drawing Sheets

METHOD AND SYSTEM FOR SIMULATING TEST INSTRUMENTS AND INSTRUMENT FUNCTIONS

CROSS-REFERENCE TO RELATED APPLICATION

This application is a continuation of U.S. patent application Ser. No. 11/514,717 filed Sep. 1, 2006 now U.S. Pat. No. 8,131,529, which claims priority under 35 U.S.C. §119(e) of U.S. provisional patent application Ser. No. 60/713,443 filed Sep. 1, 2005, both of which are incorporated by reference herein.

FIELD OF THE INVENTION

The present invention relates generally to methods and system for simulating instruments and more particularly to methods and systems for configuring a common set of electronic components to simulate a plurality of different electronic, mechanical or electro-mechanical instrument functions.

BACKGROUND OF THE INVENTION

In view of the sheer number of different instruments used in modern society, it is often desirable to simulate instruments for certain purposes, e.g., for the purpose of testing other instruments which are typically coupled to the instrument being simulated, instead of creating each instrument. A simulated instrument is alternatively referred to as a virtual instrument.

Various companies are involved in designing and producing virtual instruments, including National Instruments Corp. which has numerous patents on this topic, including U.S. Pat. Nos. 5,710,727, 5,717,614, 5,724,272, 5,784,275, 5,847,953, 5,847,955, 5,905,649, 6,173,438, 6,311,149, 6,418,392 and 6,879,926.

U.S. patent application Ser. No. 11/559,061 filed Nov. 13, 2006, now U.S. Pat. No. 8,108,191, to the same assignee, discloses apparatus to exercise electrical motor drivers by electrically simulating a geared electric or electrical motor by providing an electronic load for the power signals that are applied to it. Current levels in the load are monitored in real-time using gate array logic and digital signal processing (DSP) algorithms to determine torque, acceleration, velocity and/or position data of the motor and gear train. Motor and gear train positional signals are generated and fed back to the motor driver device to close the servo loop. Control algorithms within the gate array and DSP accurately simulate the motor inertia and act to simulate a physical motor under varying load conditions. A control interface modifies critical motor parameters such as inertia, losses, gear ratio, and loading. The '061 application is incorporated by reference herein.

In spite of the systems disclosed in these patents, it would be desirable to be able to easily or more easily configure a common set of electronic components to simulate a plurality of different electronic, mechanical or electro-mechanical instrument functions.

OBJECTS AND SUMMARY OF THE INVENTION

It is an object of the present invention to provide new methods and system for simulating instruments, particularly instruments commonly used to test units under test (UUTs) which eliminate the need to have the actual, traditional physical instrument present.

It is another object of the present invention to provide new methods and systems for configuring a common set of electronic components to simulate a plurality of different electronic, mechanical or electro-mechanical instruments or instrument functions.

In order to achieve one or both of these objects, a method and system in accordance with the invention is generally designed to configure a common set of electronic components using software in order to simulate different electronic, mechanical and/or electro-mechanical instruments or instrument functions. Simulation of an instrument or instrument function is extremely useful for functional and parametric testing of electronic assemblies, or any type of units under test, as it eliminates the need to actually have the traditional physical instrument present since testing can be performed using the synthetic simulated instrument.

For each instrument function or traditional mode of operation to be simulated, software models are created which when directed to the electronic components, cause the electronic components to respond to input in the same manner that the actual, traditional physical instrument would respond to satisfy the same test requirement input. The software models are preferably stored in a model repository which is searchable to enable a user to select the instrument function or traditional mode of operation to be simulated with the corresponding model being provided to the electronic components. Once the model, i.e., a function for each synthetic element, is downloaded and the electronic components configured according to the model functions, testing of the assemblies or other UUTs can begin. Hardware is provided to process and interpret the model(s) to result in configuration of the electronic components, with the configuration also preferably being tested to confirm compliance with the model before incorporation into the model repository for wide-scale use.

Creation of the models is subject to the structural and functional limitations of the electronic components. Accordingly, during the creation of the models, analysis of the models in consideration of these limitations is required to avoid creating a model which cannot be implemented.

A basic method for simulating a physical instrument or function of the instrument in accordance with the invention therefore includes providing a set of electronic components, at least one of which is selectively configurable, creating a software model for configuring the electronic components to simulate the instrument or instrument function, and applying the software model to the electronic components to cause the electronic components to be configured when simulation of the instrument or instrument function is desired so that the electronic components will provide a response corresponding to the simulated instrument or instrument function.

Optional enhancements to this method include creating a plurality of different software models, one for each instrument or instrument function sought to be simulated, and applying the software model corresponding to the instrument or instrument function sought to be simulated to the electronic components as desired. The software model being applied to the electronic components can be changed whenever the instrument or instrument function being simulated is changed. The software models are preferably stored in a model repository for repeated re-use. Moreover, the model repository can be networked to enable remote access thereto, e.g., by a plurality of users in different venues. Ideally, the model repository is designed to be searchable via a search engine to enable a desired software model to be easily identified and retrieved.

In one embodiment, the set of electronic components include an open source Field Programmable Gate Array (FPGA) and a processor, such as a Digital Signal Processor (DSP).

The software model may be formed as a combination of a function for each electronic component such that the software model comprises a plurality of functions, one for each of the electronic components. Tools are therefore provided to enable selection of the functions from a function repository and design of the functions for inclusion in the function repository. Design of functions may be limited based on the capabilities of the electronic component for which the function is being designed. The functions may be organized in the function repository based on common features. A function for an electronic component can be generated by identifying a target instrument, instrument function or module being simulated, analyzing the instrument to identify individual functions, grouping the identified individual functions together into a function class, and implementing a block diagram with a reconfigurable hardware design utilizing a set of design and interconnectivity rules from a repository of the software model. The function class can be partitioned based on the type of instrument.

A method for testing a unit under test (UUT) in accordance with the invention includes providing a set of electronic components, at least one of which is selectively configurable, creating a software model for configuring the electronic components to simulate instrument or instrument function, coupling the UUT to the set of electronic components, simulating the instrument or instrument function by applying the software model to the electronic components to cause the electronic components to be configured to provide a response corresponding to the instrument or instrument function associated with the software model, the response being provided to the UUT, and analyzing the reaction of the UUT to the response provided by the electronic components. The analysis can be displayed on a computer screen. The variations described in the method above can be applied to this method as well, to the extent applicable.

A system for simulating a physical instrument or function of the instrument in accordance with the invention includes a simulation module including a set of electronic components, at least one of which is selectively configurable, a data storage component including a repository of software models for configuring the electronic components to simulate the instrument or instrument function, a computer coupled to the model repository, and a user interface coupled to the computer. The computer determines which model from the model repository has been selected for use upon user control of the user interface and applies the selected model to the simulation module to cause the electronic components to be configured to simulate the instrument or instrument function so that the electronic components provide a response corresponding to the simulated instrument or instrument function.

In some embodiments, the simulation module includes an open source Field Programmable Gate Array (FPGA) and a processor, such as a Digital Signal Processor (DSP). It can also include a characterization module having additional electronic components required to simulate particular instruments. The characterization module may include signal processing circuitry, and switching circuitry to enable the FPGA and DSP to interface with the additional electronic components.

An arrangement for testing a unit under test (UUT) in accordance with the invention includes the foregoing system, a mechanism for coupling the UUT to the simulation module and the computer such that the response provided by the electronic components is directed to the UUT. The computer is arranged to analyze the reaction of the UUT to the response provided by the electronic components.

A method for creating software models for configuring electronic components to simulate an instrument or function of the instrument in accordance with the invention includes determining an initial set of electronic components to be used for simulation of the instrument or instrument function, creating a set of design and interconnectivity rules for the electronic components, determining instruments sought to be simulated or having functions sought to be simulated, analyzing each instrument to identify individual functions provided thereby, grouping the identified individual functions together into at least one function class, and developing at least one block diagram on which a function for configuring each component in the initial set is based. The function class can be partitioned based on the type of instrument. One or more additional electronic components can be added to the set of electronic components when the initial set of electronic components is unable to realize an identified individual function of the instrument.

BRIEF DESCRIPTION OF THE DRAWINGS

The following drawings are illustrative of embodiments of the invention and are not meant to limit the scope of the invention as encompassed by the claims.

DETAILED DESCRIPTION OF THE INVENTION

Figure 1:
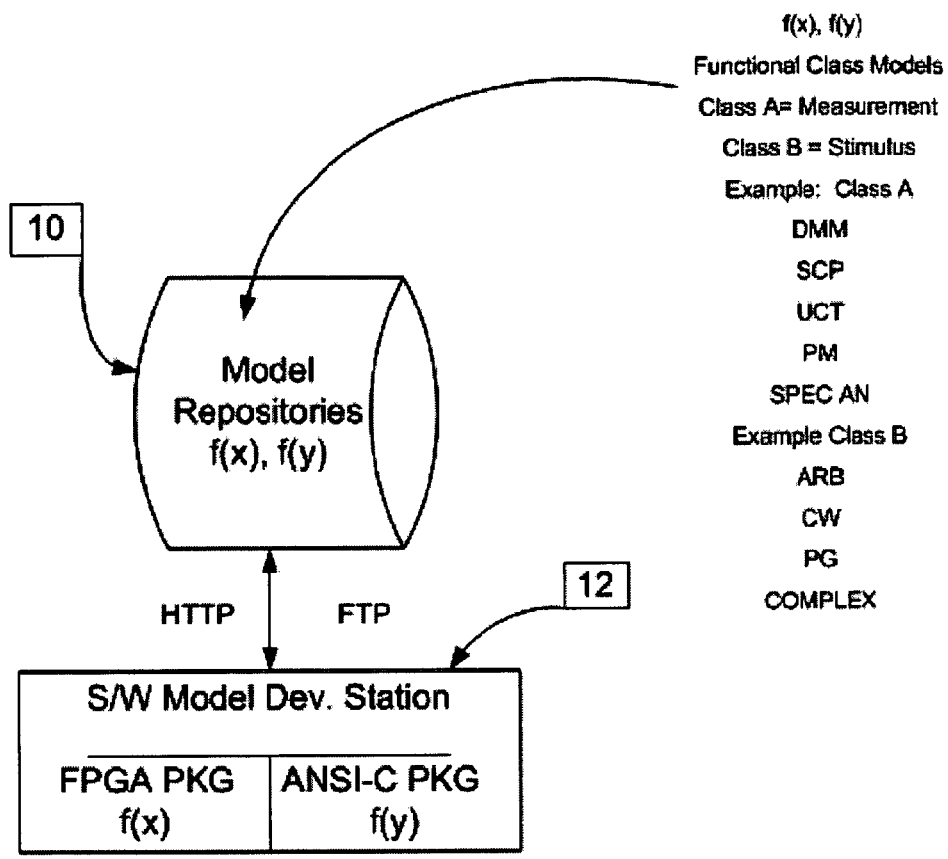
FIG. 1 is a flowchart of the hardware development environment for a system in accordance with the invention

Referring to the accompanying drawings wherein the same reference numbers refer to the same or similar elements, FIG. 1 is a flowchart of the hardware development environment for a system in accordance with the invention. The system is based on use of software models which configure electronic components to simulate or synthesize physical instruments or instrument functions. To enable multiple instruments to be simulated, model repositories are created and stored in a globally accessible memory storage unit 10. The unit 10 contains functional models to configure whatever electronic components are used in the system.

In the example described herein, the electronic components are an open source Field Programmable Gate Array (FPGA) and a Digital Signal Processor (DSP) 12. For each instrument function being simulated, a functional or encapsulated model is created which when directed to the components will cause the components to provide a response uniquely corresponding to the simulated instrument function. The functional model is a combination of a function for each component of the system, and for the described embodiment, the function for configuring or programming the FPGA is designated f(x) whereas the function for configuring or programming the DSP is designated f(y). Thus, for each instrument function to be simulated, there will be a combination of f(x) and f(y) in the model repository 10. Each encapsulated model or combination of f(x) and f(y) will therefore perform a unique function when executed in the target hardware apparatus, i.e., the set of electronic components.

Other sets of electronic components can also be used in accordance with the invention, with at least one component in the set being configurable in different ways, i.e., selectively configurable or re-configurable. Instead of a DSP, another selectively configurable processor may be used. An embedded processor may also be used, the application of which would be within the skill attributed to one skilled in the art in view of the disclosure herein. The component could thus be configured in one way when the set of electronic components is used to simulate one instrument function and in another way when the set of electronic components is used to simulate another instrument function. It is possible that the component can be configured in the same manner when simulating two different instrument functions, but this would require that one or more of the other components in the set is configured differently for the instrument function simulations. That is, it is possible that the same function might be used when simulating multiple instrument functions.

A search engine of the model repository 10 is formed and made available for use to facilitate searching, extraction, modification and addition of compiled models. The specific search criteria are based on the type of function class and test requirement parameter class.

If a model is sought for a particular instrument and no match is found, the developer can extract a similar model from the repository for modification with an appropriate toolset.

The development station may be a small computer platform capable of hosting the applicable development environments. Required development tools include a schematic capture program and an ANSI-C compiler. Both development tools must be compliant with the chipset manufacturers for the FPGA and DSP components, or other electronic components in the system.

The FPGA development environment allows the developer to design circuitry to meet the hardware requirements of their test specification. The ANSI-C development environment allows the developer to design algorithms to work in conjunction with their FPGA circuitry to meet their test specification.

Referring again to FIG. 1, the flow chart of the illustrated hardware development environment provides developers with the tools necessary to select or design hardware functions f(x) and software functions f(y) that satisfy simple and/or complex test requirements. One key to fulfilling test requirements is the open architectures of the hardware apparatus and the open source of the model repository. The tight integration of these two components is the ultimate power in solutions attainable. The combination herein allows traditional instrument functions to be implemented and at the same time, provides the test engineer with the capability to meet next generation and emerging peculiar or non-traditional test requirements.

In this section, the hardware development environment encapsulates this integration. The hardware apparatus provides the rules base for developing hardware f(x) FPGA designs and software f(y) ANSI-C procedures.

These combined functions reside in the repository. They are preferably archived by class models of measurement, stimulus and hardware in the loop. These classes can be further subdivided, for example, relative to common classic test functions. Examples of the measurement subclass are: Voltmeter, Counter-Timer, Oscilloscope, Modulation Meter, Power Meter and Spectrum Analyzer. Examples of the stimulus subclass are related to Waveform generation such as Arbitrary, Continuous, Predefined Pulse and Complex Modulations. An example of hardware in the loop is the real-time motor monitor and auto-aligning adjustment functions. The design guidelines for the generation of f(x) and f(y) groups are roughly outlined.

The process of designing a set of functions for the synthetic or simulated instrument model repository is similar for Analog, Digital and RF. The process can be broken down into functional areas and several steps. The critical functional area or component elements to consider when implementing a synthetic capability are the core control elements, i.e., f(x) and f(y), the signal conditioning and routing or distribution. The first step is to identify a target instrument, instrument function or module to be replaced or simulated and then analyze the instrument and identify individual functions thereof. The identified individual functions are grouped together into a function class, such as, waveform synthesis, waveform analysis, or in the case of digital, dynamic or static, stimulus or response.

For digital instruments or modules inclusive of communication busses, the function class is further divided into digital logic families, such as, TTL, ECL, etc., digital frequency requirements are identified along with voltage level requirements and Input and Output pin counts. Handshake requirements are also identified and then the final step is to develop block diagrams, indicating pin count, I/O Voltage levels, frequency and handshake requirements.

For analog instruments or modules, the function class is also further divided into frequency band and voltage levels.

For the function class of waveform synthesis, additional steps are required and include to identify waveform characteristics, such as input impedance, arbitrary waveforms, spectral integrity and rise and fall times, and develop block diagrams indicating frequencies, voltage levels, input impedance and waveform types supported to satisfy test requirements.

For the function class of waveform analysis, additional steps include to identify waveform characteristics to be measured such as, rise fall times, pulse width etc. . . . , and then develop block diagrams indicating frequencies, voltage levels and measurement parameters to satisfy test requirements.

For RF instruments or modules, the function class is further divided into frequency bands, power levels and complex mathematical functions.

For RF synthesis, additional steps include to identify modulations required if any, and then develop block diagrams indicating frequency requirements, power requirements and modulation requirements.

For RF analysis, additional steps include to identify a Local Oscillator (LO) frequency, identify modulations to be downconverted and then develop block diagrams indicating LO requirements, down conversion requirements, power requirements and modulation requirements.

Finally, the block diagram is implemented with a reconfigurable hardware design, utilizing a set of design and interconnectivity rules from the model repository 10.

After completion of the design, the combination of f(x) and f(y) is locked down through cyclical redundancy check algorithm and loaded into the model repository 10 for use by the runtime environment.

Figure 2:
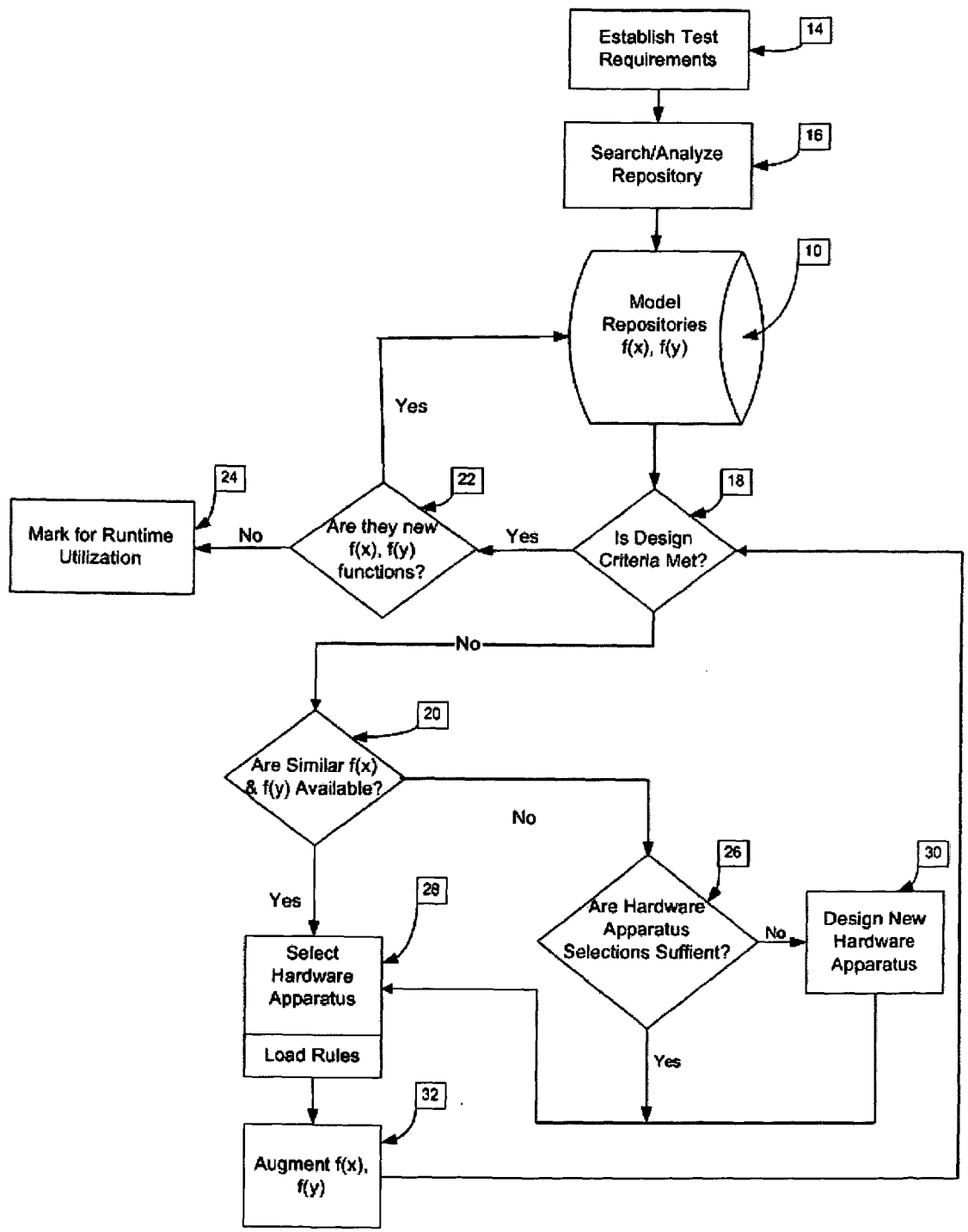
FIG. 2 is a flow chart showing how a function set which satisfies the test requirements is marked and recorded for utilization during test execution.

Referring now to FIG. 2, for any given deterministic evaluation executed on a system of Automatic Test Equipment (ATE), there is a test. In order for a test engineer to design and validate a test, the requirements for a test must be established (14). There are many means by which test requirements can be validated for design use, all of which can be applied in the invention. Test requirements can be categorized into class structures, as mentioned above with reference to the hardware development environment. Establishing test requirements is a broad part of the art of test engineering used by the test engineer to achieve the goal of an automatic test program for a given unit of test on an automated test system. Of note, the STARS tool set (sold by the current assignee) is a means by which test requirements can be mined from old electronic forms of Automated Test Programs. The ATTI BRAT® is an example of an Automated or Automatic Test System. The Program Language can be but is not limited to TBASIC®.

Once one or more test requirements are established, use of the system requires searching and/or analysis of the model repository 10 based on the test requirements established for a given test (16). To search and/or analyze the model repository 10, the test requirements may be captured in a forms-based interface. The forms-based interface may use XML technologies to conveniently allow the test engineer to design the search criteria of the model repository using, for example, drop down menus of the forms XML data accessed via a user interface coupled to a computer accessing the model repository 10. Each time a forms-based search criteria is selected or text entry is made, the resultant potential solutions are narrowed.

On selected data items on the forms, the test engineer grades how well the forms data exactly matches or meets the test requirements design criteria (18). There is an iterative process to follow to work towards exact satisfaction of test requirements. If an exact match does not already exist, a determination is made (20) as to whether any similar models are present in the model repository 10. This procedure is described more fully below.

On the other hand, following the iterative process, if the design criteria of the tests requirements are satisfied, a determination is then made (22) if new functions result. If so, those new f(x) and f(y) functions, XML test requirements data and their supporting file(s) will be committed to the model repository 10. If there are no new functions, this is indicative of a situation where the model repository includes a combination of functions f(x) and f(y) to be downloaded to the FPGA and DSP, respectively, to simulate the instrument or instrument function. Thus, once the test engineer has formed a function set which satisfies the test requirements, it is marked and recorded for utilization during test execution (24).

When a test engineer determines an acceptable match does not exist in the repository (after 18), significant effort can be reduced to satisfy the test requirement if a similar set of functions can be found (20) and modified to satisfy the test requirements. This evaluation is part of the art of being a test engineer, and can be performed by a test engineer in consideration of the disclosure herein.

Thereafter, the hardware apparatus electrical boundaries are evaluated to determine if any mandatory test requirement parameters cannot be achieved. If test requirements cannot be achieved with the existing hardware apparatus, a determination is made if they can be achieved through additional external circuitry to the apparatus in a cost tolerable manner (26). These criteria are used to determine if existing apparatus is sufficient (28) or if the design of a new and unique apparatus must be designed (30). To design new apparatus, analysis of peculiar test requirements must be classified and parameters determined such that the new apparatus adheres to the overall system.

On the other hand, if existing apparatus is sufficient, the electrical test requirements are satisfied. The design rules for modifying an existing circuit or software code segment for a selected apparatus are loaded (28). These are to be used by the test engineer when modifications are done.

Augmentation of a given circuit or code segment follows such that the encapsulated changes: a) adhere to design requirements for apparatus, b) allows for exact satisfaction of test requirements (32).

Figure 3:
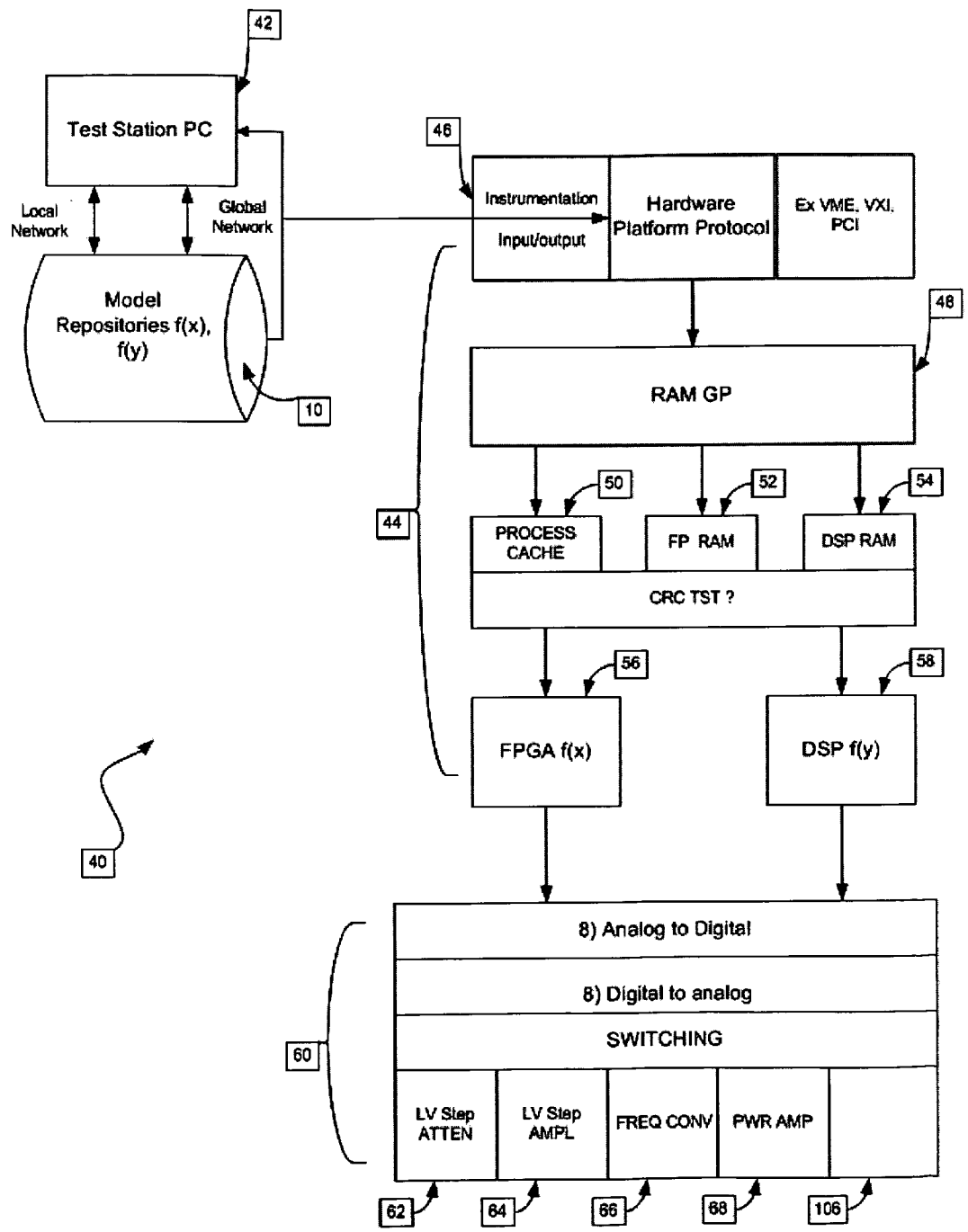
FIG. 3 shows a hardware runtime environment in a system and method in accordance with the invention.

Referring now to FIG. 3, the hardware runtime environment will now be described. Generally, in this stage, a model selected from the model repository 10 is downloaded into the electronic hardware components of the system and used to simulate the instrument function represented by the model. Use of the simulated instrument function may be desired, and preferred, for the purposes of testing assemblies or other UUTs which would otherwise be tested by the actual physical instruments. Selection of the model from the model repository 10 is obtained, for example, by a user interacting with a user interface, e.g., a keyboard or mouse, coupled to the computer or data storage unit containing the model repository 10.

An exemplifying system 40 in accordance with the invention includes a test station computer 42 which is coupled to the model repository 10. This coupling may be a direct wired connection, or a local or global network connection. Thus, the system 40 can be used at locations in proximity to the model repository 10 or remote from the model repository 10. System 40 could also be coupled to a plurality of model repositories, each in a different location, so that if a model is sought from one model repository and not found therein, another model repository could be accessed to ascertain whether the sought model is in that model repository. In this manner, a local model repository might be created with commonly used software models while a remote model repository would be created with less common software models.

The test station computer 42 is used to determine which model from the model repository 10 is to be selected for use, via use of a user interface, and to conduct the test of the assembly or other UUT using the simulated instrument or other application involving the instrument function simulated by the selected model.

Once a model is selected for use, it is directed from the model repository 10 to a simulation module 44 containing various electronic components responsive to the model such that once the components respond to the model, the components can receive input and output a response substantially identical to the expected response from the actual, traditional physical instrument provided with the same input. By being responsive to the model, it is meant that each electronic component configures, adjusts and/or controls itself based on the function corresponding to that component contained in the model.

Simulation module 44 includes an I/O section 46 receiving the model from the model repository 10, and which includes I/O instrumentation and a hardware platform protocol, such as VME, VXI and PCI, and a memory component 48, e.g., one or more RAM units. A process cache 50, FP RAM 52 and DSP RAM 54 are also provided and aid in loading of the model into the FPGA 56 and the DSP 58, specifically the loading of the function f(x) into the FPGA 56 and the loading of the function f(y) into the DSP 58. Once the functions f(x) and f(y) are loaded into the FPGA 56 and DSP 58, respectively, the simulation module 44 is ready to simulate at least those instruments functions for which software can be formed using solely an FPGA and DSP. Alternative components to the above-listed components in the simulation model 44 which perform the same, substantially the same or similar functions in the same, substantially the same or a similar manner, may also be used in the invention without deviating from the scope and spirit thereof.

Since not all instruments can be simulated using only an FPGA 56 and a DSP 58, the simulation module 44 can be provided with a characterization module 60 which includes additional electronic components necessary to simulate particular instruments. Characterization module 60 includes signal processing circuitry, e.g., analog to digital converters (ADCs) and digital to analog converters (DACs), and switching circuitry to enable the FPGA and DSP to interface with electronic components such as a low-voltage attenuator 62, a low voltage amplifier 64, a frequency converter 66 and a power amplifier 68. These electronic components are accessed as needed to simulate particular instruments as determined by the model loaded into the simulation module 44. Multiple characterization modules can be provided and each coupled to the simulation module 44 as needed. For example, the simulation module 44 can be provided with one or more coupling ports and the characterization module(s) individually or collectively attached to a respective coupling port. The attachment may be removable to enable the same coupling port to be used for different characterization modules.

Figure 4:
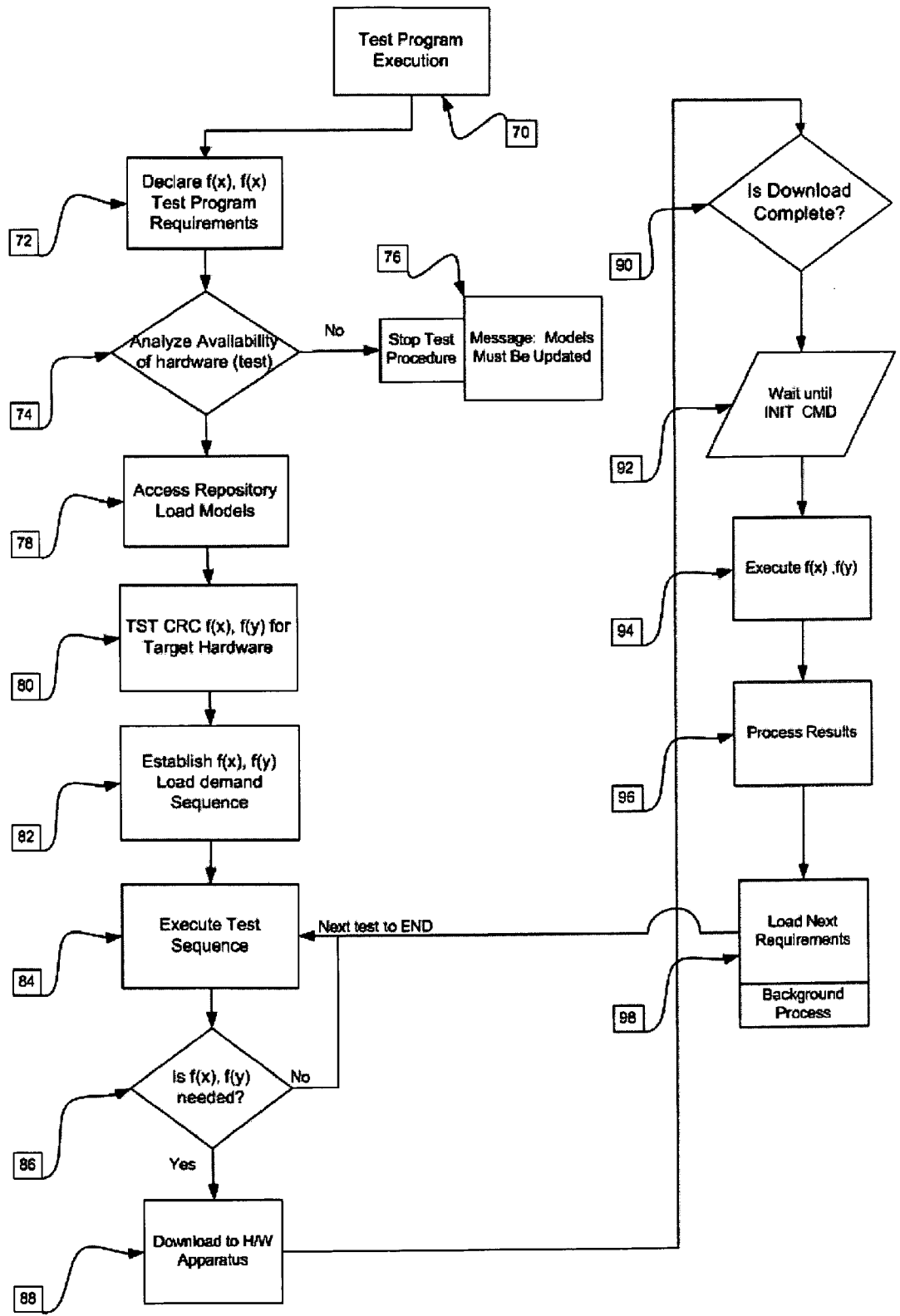
FIG. 4 shows a flow chart of the manner in which an instrument or instrument function is simulated using the hardware described in FIG. 3.

FIG. 4 shows a flow chart of the manner in which an instrument or instrument function is simulated using the hardware described in FIG. 3. Starting with the test program execution (70), test program requirements of the functions f(x) and f(y) controlling the FPGA 56 and DSP 58 respectively are declared (72) and a determination is made as to the availability of the hardware (74). If the hardware needed for the test program is not available, the test procedure is stopped and notification is provided that models must be updated to reflect the capabilities of the system (76).

When the required hardware is available, the model repository 10 is accessed and the model loaded (78). The functions of the model, f(x) and f(y) are tested for the target hardware (80), the functions are established and loaded (82) and the test sequence is executed (84). A determination is then made as to whether the functions are needed (86) and if not the test ends and the next test can begin. If the functions are needed, they are downloaded to the hardware apparatus (88), i.e., to the simulation model 44, and a determination is made as to whether the download is complete (90). After waiting for an initialization command (92), the functions are executed (94) and the results processed (96). The next test requirements are then loaded (98) followed by a subsequent text sequence execution (84).

Figure 5:
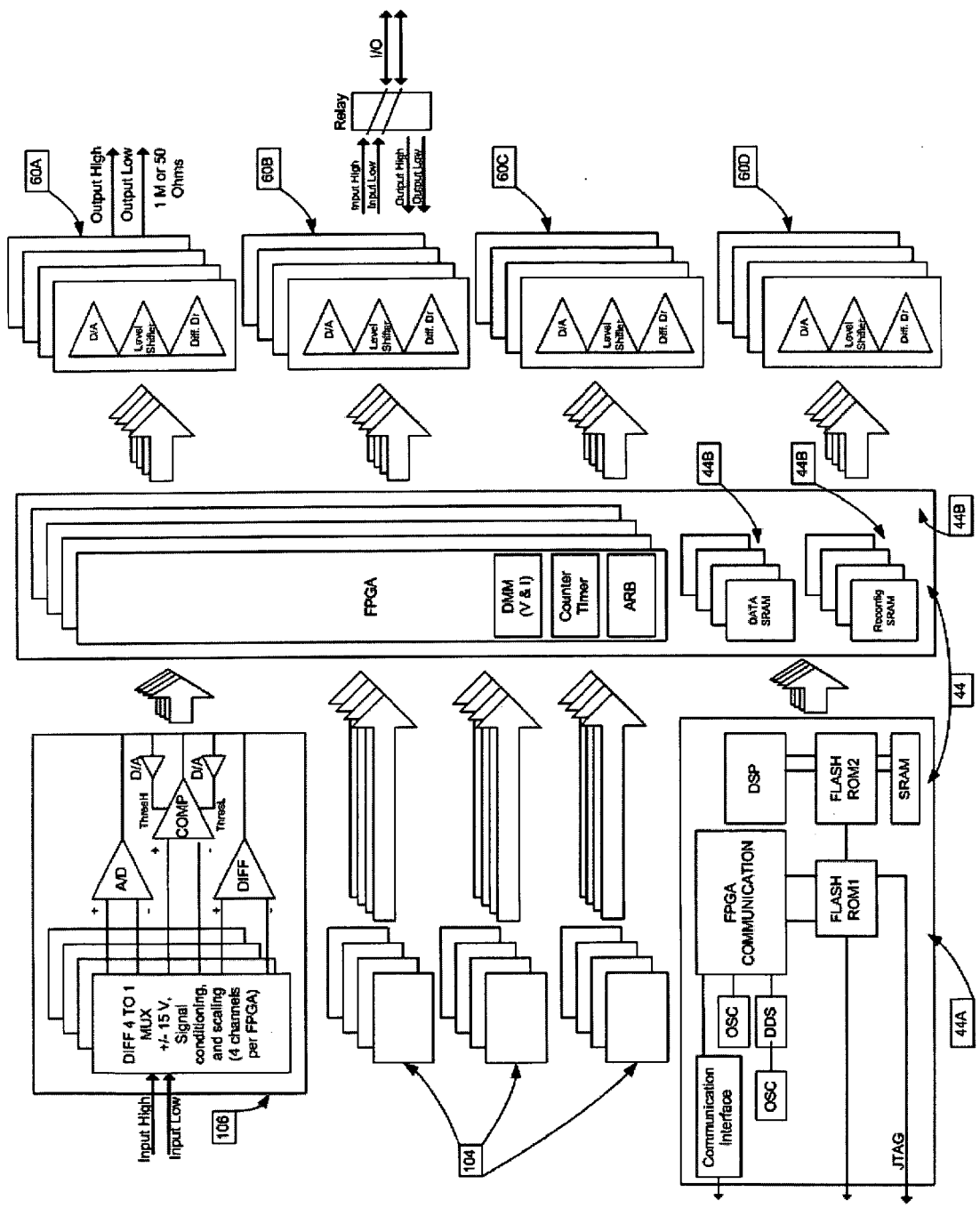
FIG. 5 shows a more detailed schematic of the hardware environment in a system and method in accordance with the invention.

Referring now to FIG. 5, in a system and method in accordance with the invention, it may be desirable to mimic multiple instruments or instrument functions within or as part of a single test. To this end, simulation module 44 is shown having a single software generation module 44A and multiple primary reprogrammable hardware modules 44B (in view of the presence of multiple arrows from the software generation module 44A and the indication of multiple FPGAs 56, data SRAMs 100 and reconfigurable SRAMs 102). With this structure, simulation module 44 can provide output to multiple characterization modules 60A, 60B, 60C, 60D from each primary reprogrammable hardware module 44B, so that when different characterization modules are used, different instrument or instrument functions can be simulated simultaneously. Additional inputs to the primary reprogrammable hardware modules 44B for use in the instrument simulation or test include inputs from various measurement devices 104 and controls for the FPGAs 56 in the primary reprogrammable hardware modules 44B from a common or a respective hardware extension 106. Hardware extension 106 is capable of multiplexing, signal conditioning, scaling and the like for the channels of the FPGAs 56 and receives input from or is part of a characterization module 60 (see FIG. 3). Additional details about the embodiment shown in FIG. 5 can be gleaned from the notations on the boxes and information relating to the notations known to those skilled in the art to which the invention pertains.

Depending on the functional capabilities of the software generation module 44A to provide programming commands to the primary reprogrammable hardware modules 44B, it is contemplated that multiple software generation modules 44A may be provided in a system and method in accordance with the invention.

In the discussion above, mention is made of instruments or instrument functions being simulated. Another way to consider the invention is as the synthesis of an instrument or instrument function from a plurality of pre-formed functions, each designed to configure or control a particular electronic hardware or software component. For example, a synthetic instrument could be formed from functions f(x) and f(y) when directed to the FPGA and DSP to configured or control them.

Having thus described a few particular embodiments of the proposed method and system, various alterations, modifications, and improvements will readily occur to those skilled in the art. For instance, the method and system can be adapted to a configuration consisting of multiple FPGAs and DSPs with minor modifications to the interface and/or schematic. Such alterations, modifications and improvements as are made obvious by this disclosure are intended to be part of this description though not expressly stated herein, and are intended to be within the spirit and scope of the proposed method and system. Accordingly, the foregoing description is by way of example only, and is not limiting. The proposed method and system is limited only as defined in the claims and equivalents thereto. In particular, the illustrated flow charts do not include all of the possible processes and characteristics for every possible instrument class as described in the specification. Rather, the flowcharts show the main steps for each instrument class in the proposed method and system.

The invention claimed is:

1. A method for synthesizing one or more of a plurality of different instrument functions to effect the instrument functions on input and provide in a run-time environment as output, a response to the input modified by the synthesized instrument function or functions, comprising:

in a development stage,
providing at least one set of electronic components, each set of electronic components including a Field Programmable Gate Array (FPGA) and a processor;
creating, using a processor, a plurality of compiled software models each for configuring a set of the electronic components to simulate a respective one of a plurality of different physical instruments, different functions of the same instrument or functions of the instruments,
the step of creating the software models comprising forming, using a processor, each of the plurality of software models with two different functions, f(x) and f(y), wherein
f(x) is a function that configures only the hardware of the set of electronic components including the FPGA; and
f(y) is a function that configures software for the synthesized instrument function and is dependent on the hardware of the set of electronic components including the FPGA that is configured by f(x), f(x) and f(y) being formed such that when f(x) is applied to the hardware including the FPGA and f(y) is applied to the processor, the hardware including the FPGA configured based on f(x) is controlled in accordance with software procedures based on f(y) and the electronic components will provide a response to input that corresponds to the simulated instrument or instrument function operative on the input, f(x) and f(y) being formed for each of the plurality of software models such that the software models are different from one another; and storing the plurality of software models in a plurality of model repositories such that each of the model repositories contains at least one of the software models, each including a single function f(x) and a single function f(y) formed based on that function f(x); and in a run-time stage, enabling a user to access the model repositories via a network and select any one of the plurality of stored software models from the model repositories when simulation of the instrument or instrument function is desired; and applying the selected software model to the associated set of electronic components to cause the electronic components to be configured when simulation of the instrument or instrument function is desired so that the electronic components will provide the response corresponding to the simulated instrument or instrument function, the step of applying the selected software model comprising:

directing the function f(x) of the selected software model to the hardware of the set of electronic components including the FPGA; and directing the function f(y) of the selected software model to the processor.

2. The method of claim 1, further comprising changing the software model being applied to the electronic components whenever the instrument or instrument function being simulated is changed.

3. The method of claim 1, further comprising:

networking the model repositories to enable remote access thereto;

at a remote site of the set of electronic components, identifying an instrument or instrument function for which a software model is sought to be applied to the set of electronic components;

accessing at least one of the model repositories via the network to retrieve one of the plurality of software models having two different functions f(x) and f(y); and applying the functions f(x) to the FPGA and the function f(y) to the processor to thereby simulate the identified instrument or instrument function for the set of electronic components.

4. The method of claim 1, further comprising enabling searching of the model repositories via a search engine.

5. The method of claim 1, further comprising forming the functions f(x) and f(y) to provide specific hardware functionality of the simulated instrument or instrument function.

6. The method of claim 1, further comprising forming the software model as a combination of a function for each electronic component in the set of electronic components including the function f(x) for the FPGA and the function f(y) for the processor such that the software model comprises a plurality of functions, one for each of the electronic components.

7. The method of claim 6, further comprising providing tools to enable selection of the functions from a function repository and design of the functions for inclusion in the function repository.

8. The method of claim 6, further comprising limiting design of functions based on capabilities of the electronic component for which the function is being designed.

9. The method of claim 7, further comprising organizing the functions in the function repository based on common features.

10. The method of claim 6, further comprising:

generating a function for an electronic component by identifying a target instrument, instrument function or module being simulated, for each identified target instrument, analyzing the instrument to identify individual functions of the instrument, grouping the identified individual functions of the instrument together into a function class, and implementing a block diagram with a reconfigurable hardware design utilizing a set of design and interconnectivity rules from one of the model repositories.

11. The method of claim 10, further comprising partitioning the function class based on the type of instrument.

12. The method of claim 1, wherein the user is enabled to access the model repositories using a test station computer, further comprising conducting a test of a unit under test coupled to the set of electronic components using the test station computer while the selected software model is applied to the set of electronic components.

13. A method for testing a unit under test (UUT), comprising:

in a development stage, providing at least one set of electronic components, each set of electronic components including a Field Programmable Gate Array (FPGA) and a processor;

creating, using a processor, a plurality of compiled software models each for configuring a set of the electronic components to simulate a respective instrument or instrument function;

the step of creating the software models comprising forming, using a processor, each of the plurality of software models with two different functions, f(x) and f(y), wherein f(x) is a function that configures only the hardware of the set of electronic components including the FPGA; and f(y) is a function that configures software for the processor and is dependent on the hardware of the set of electronic components including the FPGA that is configured by f(x), f(x) and f(y) being formed such that when f(x) is applied to the hardware including the FPGA and f(y) is applied to the processor, the hardware including the FPGA configured based on f(x) is controlled in accordance with software procedures based on f(y) and the electronic components will provide a response to input that corresponds to the simulated instrument or instrument function operative on the input, f(x) and f(y) being formed for each of the plurality of software models such that the software models are different from one another; and storing the plurality of software models in a plurality of model repositories such that each of the model repositories contains at least one of the software models, each including a single function f(x) and a single function f(y) formed based on that function f(x); and in a run-time stage
coupling the UUT to the set of electronic components;
enabling a user to access the model repositories via a network using a test station computer and select any one of the plurality of stored software models from the model repositories when simulation of the instrument or instrument function is desired;
applying the selected software model to the associated set of electronic components to cause the electronic components to be configured to provide the response corresponding to the instrument or instrument function associated with the software model, the response being provided to the UUT,
the step of applying the selected software model comprising:
directing the function f(x) of the selected software model to the hardware of the set of electronic components including the FPGA; and
directing the function f(y) of the selected software model to the processor; thereafter
conducting a test of the UUT using the test station computer while the selected software model is applied to the set of electronic components; and then
analyzing the reaction of the UUT to the response provided by the electronic components.

14. The method of claim 13, wherein the test station computer is configured to provide the selected software model to the set of electronic components, provide input to the configured set of electronic components and direct output from the configured set of electronic components to the unit under test.

15. A system for synthesizing one or more of a plurality of different instrument functions to effect the instrument functions on input and provide as output, a response to the input modified by the synthesized instrument function or functions, comprising:
a simulation module including at least one set of electronic components, each set of electronic components including a Field Programmable Gate Array (FPGA) and a processor;
a data storage system including a plurality of repositories of compiled software models, each of said software models configuring a set of said electronic components to simulate a respective one of the plurality of different physical instruments, different functions of the same instrument or functions of the instruments, each of said model repositories including at least one software model,
each of the plurality of software models including a single function f(x) and a single function f(y) formed based on that function f(x), wherein
f(x) is a function that configures only the hardware of the set of electronic components including the FPGA; and
f(y) is a function that configures only software for the processor and is dependent on the hardware of the set of electronic components including the FPGA that is configured by f(x), f(x) and f(y) being formed such that when f(x) is applied to the hardware including the FPGA and f(y) is applied to the processor, the hardware including the FPGA configured based on f(x) is controlled in accordance with software procedures based on f(y) and a response corresponding to the simulated instrument or instrument function is provided,
f(x) and f(y) being formed for each of the plurality of software models such that the software models are different from one another;
a computer coupled to said model repositories via a network; and
a user interface coupled to said computer and that enables a user, in a run-time stage, to access the repositories and select any one of the plurality of software models stored in said data storage system when simulation of an instrument or instrument function is desired, said computer determining which model from said model repositories has been selected for use upon user control of said user interface and applying the selected model to said simulation module to cause the associated set of said electronic components to be configured to simulate the instrument or instrument function so that said electronic components provide the response corresponding to the simulated instrument or instrument function, said computer applying the selected software model by directing the function f(x) of the selected software model to the hardware of the set of electronic components including the FPGA, and directing the function f(y) of the selected software model to the processor.

16. The system of claim 15, wherein the functions f(x) and f(y) are formed to provide specific hardware functionality of the simulated instrument or instrument function.

17. The system of claim 15, wherein said simulation module includes at least one characterization module each having additional electronic components required to simulate a particular instrument, each of said at least one characterization module including signal processing circuitry, and switching circuitry to enable the FPGA and processor to interface with said additional electronic components.

18. An arrangement for testing a unit under test (UUT), comprising:
the system of claim 15,
a system that couples the UUT to said simulation module and said computer such that the response provided by said electronic components is directed to the UUT, said computer being configured to analyze the reaction of the UUT to the response provided by said electronic components.

19. A method for creating in a development stage, a plurality of different software models for configuring different sets of electronic components to simulate in a run-time stage, instruments or functions of the instrument, comprising:
providing a plurality of different electronic components;
selecting from the plurality of different electronic components, an initial set of electronic components to be used for simulation of the instrument or instrument function, the initial set including a Field Programmable Gate Array (FPGA) and a processor;
determining instruments sought to be simulated or having functions sought to be simulated;
analyzing each instrument to identify individual functions provided thereby;
grouping the identified individual functions together into at least one function class;
developing at least one block diagram on which a function for configuring each component in the initial set is based;
implementing the developed at least one block diagram with a reconfigurable hardware design utilizing a set of design and interconnectivity rules for the electronic components wherein each software model includes two different functions, f(x) and f(y), and f(x) and f(y) are formed for each of the software models such that the software models are different from one another, wherein f(x) is a function that configures only the hardware of the set of electronic components including the FPGA and f(y) is a function that configures only software for the processor and is dependent on the hardware of the set of electronic components including the FPGA that is configured by f(x), f(x) and f(y) being formed such that when f(x) is applied to the hardware including the FPGA and f(y) is applied to the processor, the hardware including the FPGA configured based on f(x) is controlled in accordance with software procedures based on f(y) and the response corresponding to a simulated instrument or instrument function is provided; then selecting from the plurality of different electronic components, at least one additional set of electronic components to be used for simulation of a different instrument or instrument function and for each at least one additional set of electronic components, determining instruments sought to be simulated or having functions sought to be simulated;

analyzing each instrument to identify individual functions provided thereby;

grouping the identified individual functions together into at least one function class;

developing at least one block diagram on which a function for configuring each component in the at least one additional set is based; and implementing the developed at least one block diagram with a reconfigurable hardware design utilizing the set of design and interconnectivity rules for the electronic components; and then storing the software models in a plurality of model repositories such that each of the model repositories contains at least one of the software models, the model repositories being situated in a memory storage unit that is accessible via a network or at different locations.

20. The method of claim 19, further comprising partitioning the function class based on the type of instrument.

21. The method of claim 19, further comprising adding one or more additional electronic components to the set of electronic components when the initial set of electronic components is unable to realize an identified individual function of the instrument.

\* \* \* \* \*